United States Patent [19]

Shober, Jr. et al.

[11] Patent Number: 5,279,583

[45] Date of Patent: Jan. 18, 1994

[54] RETRACTABLE INJECTION NEEDLE ASSEMBLY

[76] Inventors: Robert C. Shober, Jr., P.O. Box 143, Alvaton, Ky. 42122; Robert L. Watson, 1600 Singletree Way, Bowling Green, Ky. 42103

[21] Appl. No.: 936,338

[22] Filed: Aug. 28, 1992

[51] Int. Cl.⁵ .............................................. A61M 5/00
[52] U.S. Cl. ........................................ 604/198; 604/411; 604/414; 604/905
[58] Field of Search ............... 604/198, 263, 192, 86–91; 604/283; 604/284; 604/411–415, 905; 141/328, 329

[56] References Cited

U.S. PATENT DOCUMENTS 4,834,149  5/1989  Fournier et al. ............... 604/905 X
4,834,152  5/1989  Howson et al. ............... 604/905 X
4,872,494  10/1989  Coccia ............................ 604/905 X Primary Examiner—John D. Yasko
Attorney, Agent, or Firm—Walter C. Farley

[57] ABSTRACT

A needle shielding and use-facilitating apparatus has a first sleeve with a coupling at one end for attachment to a syringe and a hypodermic needle carried by the first sleeve. The needle extending beyond the opposite end of the first sleeve. A second sleeve is slidably received in the first sleeve and surrounds part of the needle which extends beyond the first sleeve. A spring in the first sleeve urges the second sleeve out of the first sleeve. An end coupling is attached to the second sleeve and is selectively attachable to any of a plurality of articles puncturable with the needle.

9 Claims, 5 Drawing Sheets

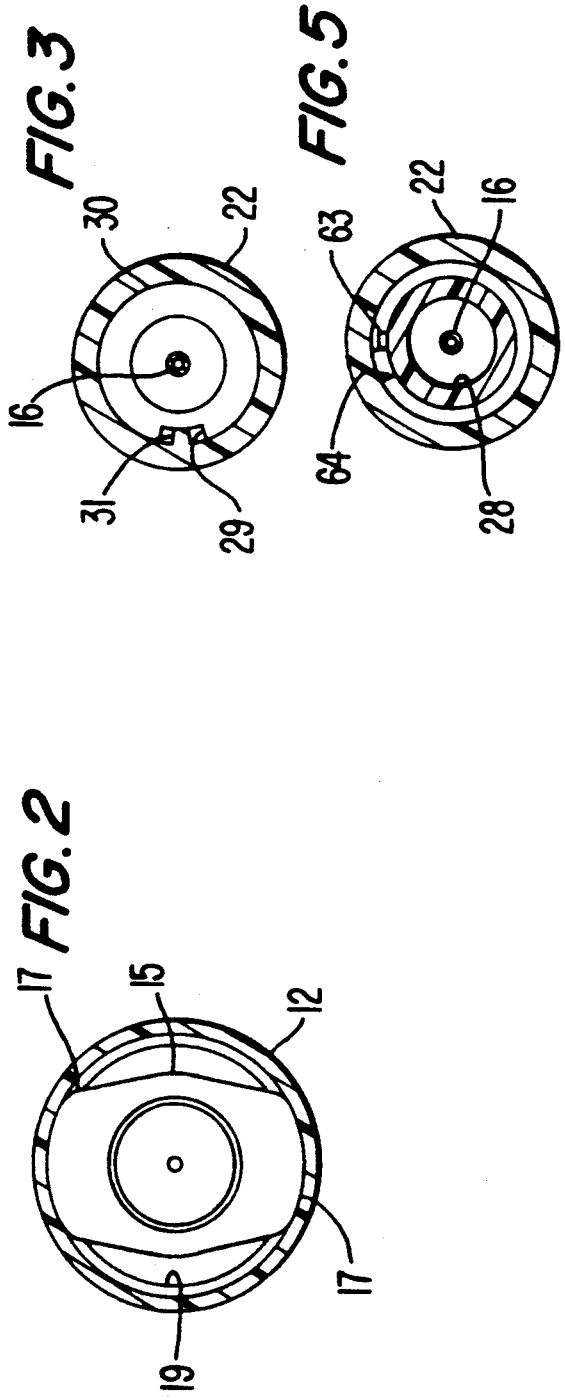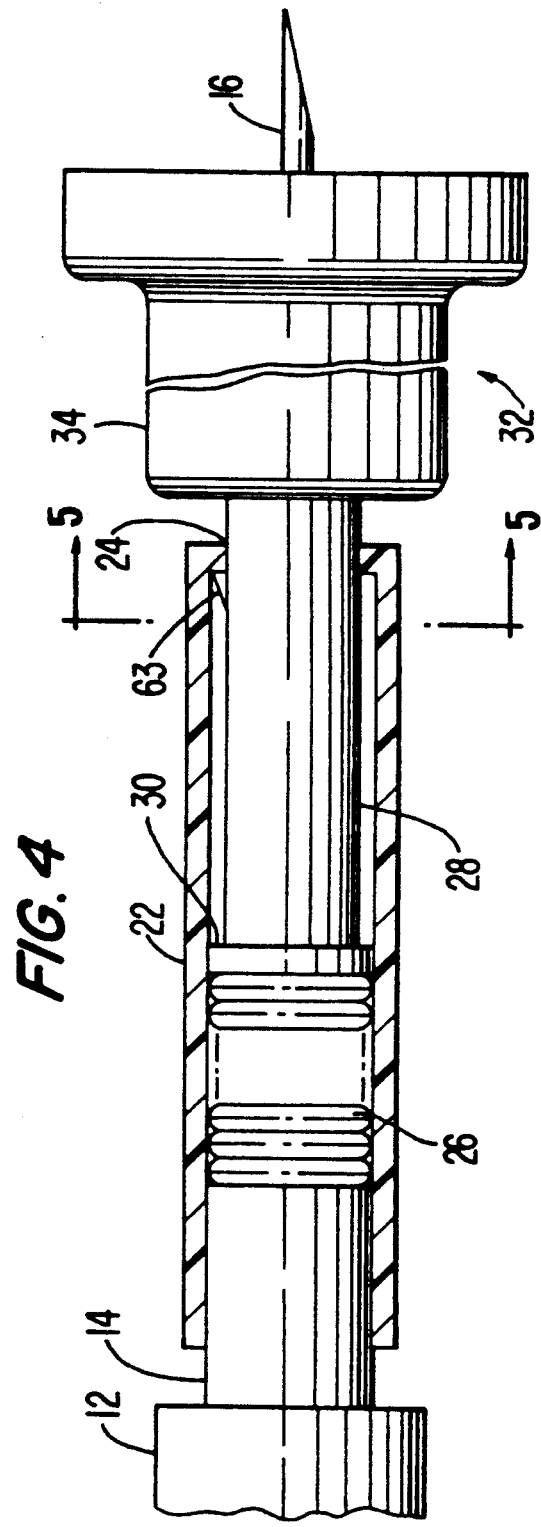

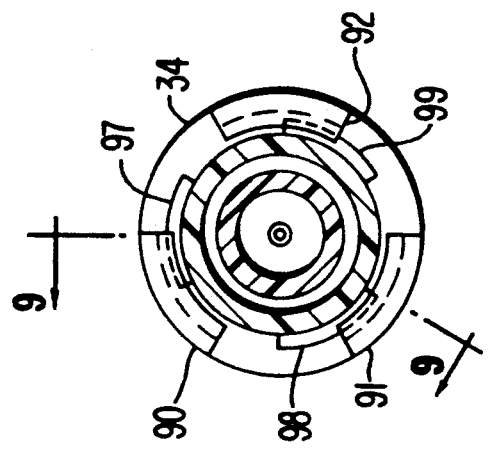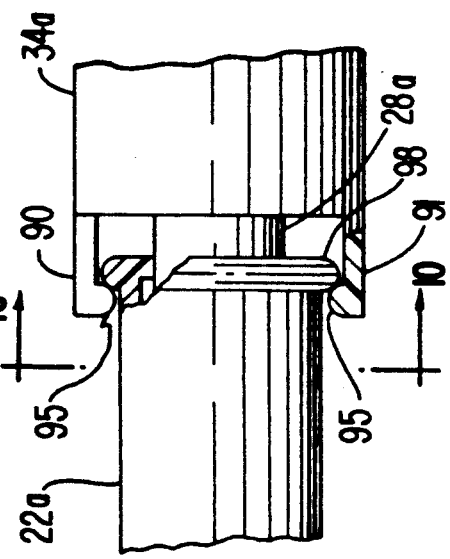

RETRACTABLE INJECTION NEEDLE ASSEMBLY

FIELD OF THE INVENTION

This invention relates to a safety apparatus for holding a needle in an assembly which protects a physician or nurse from accidental puncture by a needle but exposes the needle when needed for medical uses of various kinds.

BACKGROUND OF THE INVENTION

In recent years attention in the medical field has been directed to the prevention of the transmission of infectious diseases through normal contact with patients. Only recently has the medical profession become acutely concerned with transmission of infectious diseases from the patient to the health care personnel, and vice versa, during routine treatment. In particular, the medical profession is now actively considering new techniques and devices to prevent the accidental transmission of the HIV virus (AIDS), hepatitis and other blood-borne diseases between the health care personnel and patients.

In several instances, doctors and nurses have contracted hepatitis or the AIDS virus by accidentally puncturing a finger, hand or other body part with a hypodermic needle which has been in contact with a patient infected with hepatitis or the AIDS virus. One of the more common manners in which health care personnel are at risk and have become infected is during injection with a hypodermic needle when the needle slips or breaks and is accidentally plunged into the hand of the person administering the care. Accidents have occurred during injection directly into the patient and also during injection into the coupling of an IV tube.

It is common practice to administer drugs to a patient by inserting a syringe with a needle into a y-shaped coupling in the IV supply tube. This operation typically requires forcing the hypodermic needle with one hand through a puncturable septum in the coupling while the coupling is held with the other hand. The coupling is usually quite small and difficult to handle, thereby creating a high risk of injuring the operator while attempting to insert the needle and when replacing the safety cap on a used needle.

Whether or not there is a serious risk of transmitting a disease, it is desirable to find ways to prevent injury to medical personnel during the always risky procedures concerning the handling and use of exposed needles whether the needle is being used to add medications to an IV, extract a medication from a bottle, administer intramuscular injections, or perform any one of several other needle-related operations.

SUMMARY OF THE INVENTION

Accordingly, an object of the present invention is to provide an apparatus which safely holds a needle of a type used for injections and the like so that the point thereof is substantially enclosed until it is needed, whereupon it an be exposed to a useful position and employed to penetrate a membrane or the like to convey fluids and that after use is automatically returned to the enclosed position, shielding the tip of the needle.

Briefly described, the invention comprises a needle shielding and use-facilitating apparatus comprising a first sleeve having means at one end thereof for attachment to the output end of a syringe. A hypodermic needle carried by the first sleeve has a lumen therethrough communicating at said one end with the syringe, the other end being pointed and extending beyond an opposite end of the first sleeve. A second sleeve has a first end telescopically and slidably received in said opposite end of the first sleeve. The second sleeve surrounds the end portion of the needle which extends beyond the opposite end, the second sleeve being movable between a first position in which the end portion is totally enclosed within the second sleeve and a second position in which part of said end portion protrudes beyond the second end of the second sleeve. A spring within the first sleeve urges the second sleeve tot he first position. An end coupling is attached to the second end of, and is movable with, the second sleeve and has means for attaching selectively to any one of a plurality of articles either penetratable with the needle or coupled thereto, the length of the second sleeve being selected so that the pointed needle end extends into the end coupling in the second position whereby a membrane in the selected article is puncturable by the needle.

BRIEF DESCRIPTION OF THE DRAWINGS

In order to impart full understanding of the manner in which these and other objects are attained in accordance with the invention, particularly advantageous embodiments thereof will be described with reference to the accompanying drawings, which form a part of this disclosure, and wherein:

FIG. 2 is a transverse sectional view along line 2—2 of FIG. 1;

FIG. 3 is a transverse sectional view along line 3—3 of FIG. 1;

FIG. 4 is a partial side elevation of the apparatus of FIG. 1 with the internal spring thereof compressed and the needle extended;

FIG. 5 is a sectional view along line 5—5 of FIG. 4;

FIG. 9 is a partial side elevation of an apparatus in accordance with the invention showing a latching mechanism usable therein in partial section along line 9—9;

FIG. 10 is a transverse sectional view along line 10—10 of FIG. 9;

FIG. 11 is a partial side elevation of a sleeve assembly in accordance with the invention showing a rotation controlling mechanism.

DESCRIPTION OF THE PREFERRED EMBODIMENTS

Figure 1:
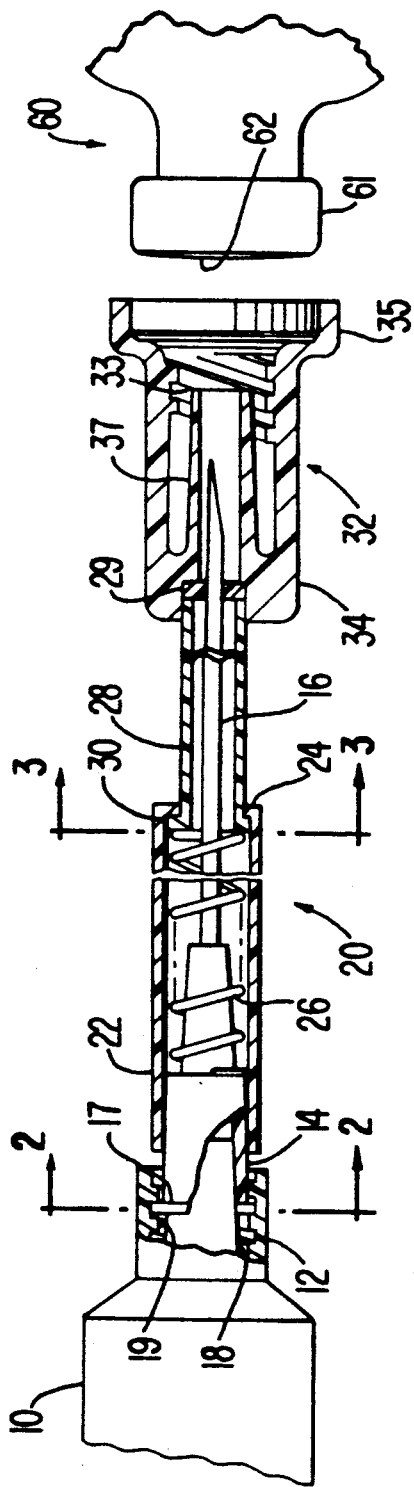
FIG. 1 is a partial foreshortened side elevation, in partial section, of an apparatus in accordance with the invention.

The apparatus of the invention will first be described with reference to FIGS. 1-4 in conjunction with a convention syringe 10 of a type having an internally threaded fitting 12 at the end thereof of a type sold under the trademark Luer-Lok®, a registered trademark of becton, Dickinson & Company, Rutherford, NJ. As shown in FIG, 2, this kind of threaded collar 12 is designed to receive the proximal end of a plastic fitting 14 holding an injection needle 16, i.e., a hollow needle of the type used to extract blood from a patient, inject medications hypodermically or intravenously, and inject medications into fittings employed for intravenous delivery with other fluids, among other uses. Needles of various sizes are normally provided with a fitting similar to fitting 14 fixedly attached to the proximal end of the needle to facilitate connection of the needle to various devices such as syringes and the like. The proximal end 15 of fitting 14 has flanges 17 protruding in opposite directions, the peripheries of the flanges being dimensioned to be received between the lands of threads 19 within collar 12. A central spout or nipple 18 extends axially from the syringe within the threaded collar and frictionally engages a tapered interior surface of fitting 14, producing a tight fit which, in conjunction with the threads, holds the needle fitting in place and also provides a fluid-tight seal so that fluids from within the syringe 10 can be forced through the lumen of the needle. Fitting 14 also has a conical outer surface for frictionally engaging a cover or the like. Generally, the portion of the Luer-Lok ® fitting having the collar and flange is regarded as the male portion while that with the tapered interior surface and the flanges, like fitting 14, is regarded as the female portion.

This kind of threaded fitting and needle assembly is very frequently, if not universally, used to attach a needle to a syringe. The needle initially arrives from the manufacturer in a rigid safety sleeve, not shown, which encases the needle and frictionally engages the outside of fitting 14, the needle ad sleeve being contained in a sterile package. When it is time to use the needle, the outer package is removed and flanges 17 are inserted into collar 12 and rotated to engage threads 19 and lock the needle fitting onto the syringe. The safety sleeve is then pulled off, exposing the needle for use. The needle is a conventional needle in the sense that is hollow and has a slanted end terminating in a very sharp point to facilitate penetration of skin or a rubber or plastic membrane, as necessary.

It should be mentioned that the Luer-Lok ® type of connector is used to interconnect many other types of devices commonly employed to convey fluids to and away from a patient including valves, pressure transducers and tubes of various kinds.

An assembly 20 in accordance with the present invention includes a tubular spring sleeve 22 which is substantially cylindrical, the inner diameter of the proximal end of sleeve 22 being selected to frictionally engage the outer conical surface of fitting 14. The distal end of sleeve 22 is formed with an inwardly extending flange 24. Within sleeve 22 is a compression coil spring 26.

The proximal end of a generally tubular needle-encasing sleeve 28 is received within sleeve 22 and is axially slidable therein, the proximal end of sleeve 28 having an outwardly extending flange 30 which engages flange 24 to prevent sleeve 28 from completely emerging from sleeve 22. As will be recognized, one end of spring 26 engages fitting 14 and the other end thereof abuts flange 30, the length of the spring being selected so that it urges flanges 24 and 30 into abutment with each other. Thus, sleeve 28 is telescopically movable between a first position shown in FIG. 1 in which flanges 24 and 30 are in abutment and a second position in which those flanges are spaced apart and spring 26 is compressed. In the second position (shown in FIG. 4), sleeve 28 is almost entirely contained within sleeve 22.

Attached to the distal end of sleeve 28 is an end coupling or bell indicated generally at 32 having a first, internally threaded portion 34 and a larger unthreaded skirt portion 35. Bell 32 is provided with a recess to receive the distal end of sleeve 28 and also a rubber diaphragm 29 which extends transversely across the end of sleeve 28 and is penetrated by needle 16 to form a seal preventing the flow of fluid from the bell into the interior of sleeve 28. The distal end of sleeve 28 is fixedly attached to bell 32 by an adhesive or by heat fusion of the members together. Portion 34 is formed substantially like fitting 12 in the sense that it has the same internal diameter and similarly formed internal threads 33 for the purpose of connection to a fitting like fitting 14, if desired, which may be attached to a needle or to some other fluid-conducting device. In addition, a spout 37 extends axially into the interior of threaded portion 34 to engage the interior of a needle fitting in the same manner as spout 18 engages the inner surface of fitting 14. In this manner, the bell is connectable to a needle in a manner similar to a Luer-Lok ® fitting, to a stop cock or to a depressable valve assembly.

FIG. 3 is a sectional view illustrating a slot and key arrangement to limit or prevent relative rotation between sleeves 22 and 28. Flange 30 is formed with an axially extending slot 29 about 3 mm in width which slidably mates with an elongated key 31 having a width of about 1 mm formed on and extending axially along the inner surface of sleeve 22. With this slot and key coupling the two sleeves together, it is possible to rotate syringe 10 and, after a small amount of rotation to take up the lost motion, thereby also rotate bell 32. This is a considerable convenience when one hand is holding a fitting to which bell 32 is to be connected and the other hand is holding the syringe; by merely rotating the syringe, the components are joined without the need to separately grasp and turn sleeve 28 or the bell. Alternatively, the flange 30 can be formed with a radially extending key and sleeve 22 with a slot to receive the key.

Figure 6:
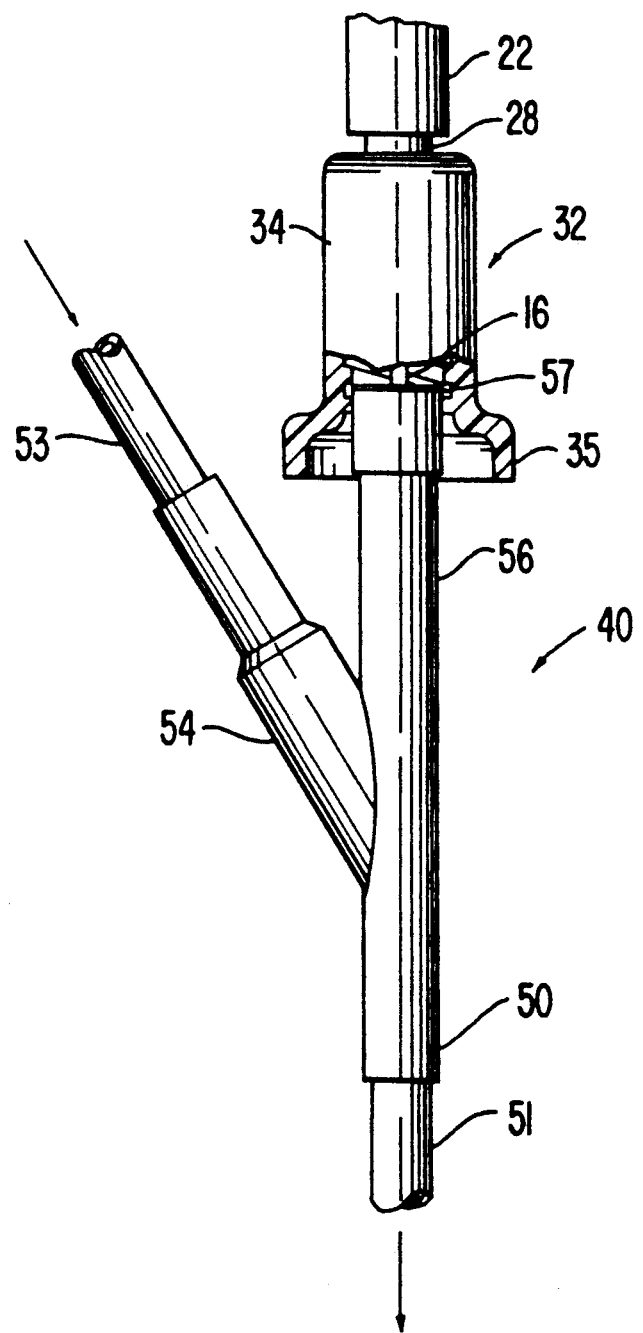
FIG. 6 is a schematic view of a portion of the apparatus of FIGS. 1-4 in use in conjunction with a conventional Y-connector.

Bell 32 is also connectable to a fitting for adding medication, by syringe, to an intravenous (IV) arrangement using a Y-connector which is commonly employed for this purpose. A typical arrangement is shown in FIG. 6 wherein the Y-fitting indicated generally at 40 has an output leg 50 connected to a tube 51 which would typically lead to a patient. An input tube 53 is connected to an input leg 54 of the Y-fitting and a supplementary leg 56 is available for the addition of medications, supplementing the fluid delivered from a saline bag or the like through tube 53. The upper end 57 of leg 56 is closed by a transverse rubber diaphragm which can be punctured by a needle attached to a syringe for adding this medication.

Problems frequently arise when a medical attendant seeks to push an exposed needle attached to a syringe through the diaphragm 57 because the Y-fitting is normally held in one hand as the attendant guides the needle and there is nothing to prevent the needle from stabbing the holding hand if it should miss or be deflected from leg 56. With the apparatus of the present invention, however, bell 32 is dimensioned at the end of portion 34 to surround and partly engage the end of leg 56, enclosing the diaphragm. Bell 32 is then rotated, causing threads 33 to securely fix the bell to the rubber-cased (or Luer-Lok ® fitted) port and centering the needle with respect to the diaphragm. The needle can then be pushed into the diaphragm, compressing spring 26 as shown in FIG. 4. The spring force is chosen so that the frictional engagement of needle 16 with diaphragm 57 is sufficient to keep spring 26 compressed, allowing fluids to be injected into the Y-fitting as needed.

FIG. 4 also shows a latching arrangement for holding the sleeves in the telescoped position. As mentioned above, the force of spring 26 is preferably chosen so that the frictional engagement of needle 16 in a releasable rubber diaphragm is sufficient to keep the sleeves telescoped in the second position. However, that force selection is not always an exact process and can change from spring to spring. Also, there are times when it is desirable to keep the apparatus in the second position without the needle penetrating a resealable diaphragm. For this purpose, the exterior surface of sleeve 28 is provided with an outwardly protruding tooth 63 on a side of the sleeve. This tooth is about 1 mm in width (as measured perpendicular to the axis of the sleeve) and has a gently sloping surface facing away from bell 32 and a somewhat more abrupt radial shoulder facing the bell. Sleeve 22 is made of a plastic material of sufficient flexibility to permit inwardly extending flange 24 to deform radially enough to pass over the tooth as spring 26 is compressed and the sleeves are telescoped to the position shown in FIG. 4. When the sleeves are telescoped sufficiently, the flange passes over the apex of the tooth, returns to its original shape and retains the sleeves in the telescoped position. A notch 64 (FIG. 5) having a width of slightly more than 1 mm can be provided in flange 24 so that slight rotation of sleeve 28 relative to sleeve 22 aligns slot 64 with tooth 63, allowing release of the latch, whereupon spring 26 returns the sleeves to their extended position. Although somewhat exaggerated in FIG. 4 for clarity, tooth 63 is preferably formed so that it protrudes minimally from the surface of sleeve 28 having a radial dimension on the order of 0.5 mm.

As illustrated in FIG. 1, an enlargement 34 may be formed at the end of the bell to fit over the top of a conventional medication vial indicated generally at 60. A vial of this type generally has a metal top 61 which holds a resealable rubber diaphragm 62 across the end of the vial. To remove medication for delivery to a patient, a needle is pushed through the diaphragm and a syringe attached to the needle is pulled to extract the medication from the vial. To avoid the possibility of injury to the person performing this task, enlargement 35 is positioned on the bottle top, properly centering the needle for insertion through the diaphragm. This substantially eliminates the possibility that the needle might slip to one side and stick the user.

It is also possible to provide additional enlarged skirts at the end of the bell 32, but such additions tend to make the bell more cumbersome and raise the possibility that they will interfere with connections to other devices such a valves and the like.

Figure 7:
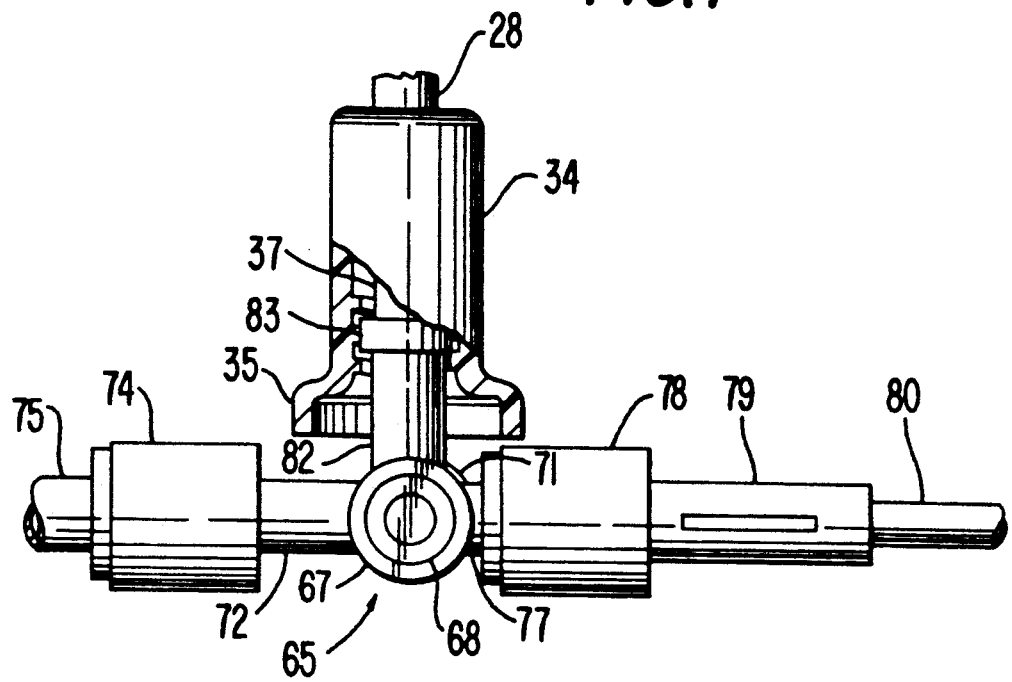
FIG. 7 and 8 are opposite side elevations of an apparatus in accordance with the invention used in conjunction with a conventional valve assembly for sampling fluids from a conduit.
Figure 8:
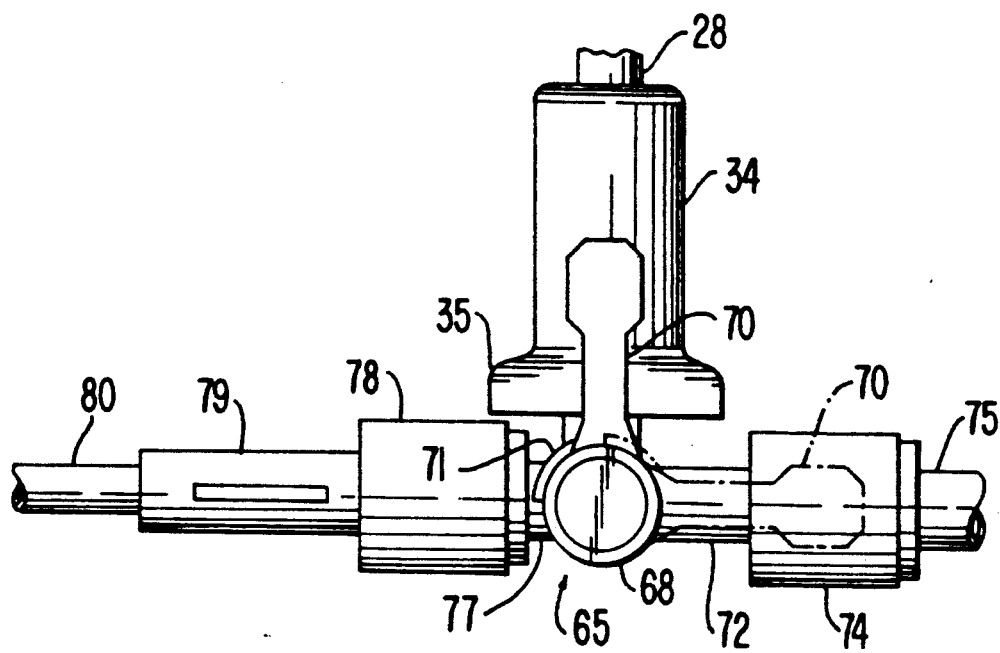

A connection to a valve is shown in FIGS. 7 and 8 wherein the apparatus is shown in two side elevations from opposite sides. The valve, indicated generally at 65, is a conventional device which can be connected into a tubing arrangement to control the flow of the fluid and to permit sampling of the fluid using a syringe and needle. The valve illustrated has a central body 67 containing a cylindrical valve body 68 which has a T-shaped passage therethrough and which is rotatable about an axis perpendicular to the paper in FIGS. 7 and 8. A handle 70 is connected to the valve body and is movable between positions shown in solid and phantom lines in FIG. 8 to rotate the valve body between two orthogonal rotary positions. A stop member 71 is attached to and is rotatable with valve body 68 and cooperates with fixed stops on central body 67 to limit the rotary motion of the valve.

At one side of valve body (stopcock) 67 is a first stem 72 which terminates in a flange of a Luer-Lok ® coupling, shown in the FIGS. attached to a threaded sleeve 74 of the coupling which is attached to a tube 75. At the other side of central body 67 is a second stem 77 having a threaded coupling sleeve 78 attached thereto, the sleeve being connected to a flanged coupling member 79 which is attached to a tube 80.

At the top of central body 67 is a third stem 82 having a flange 83 at the upper end thereof for attachment to a coupling sleeve which, in the FIGS., is bell 32 of a device in accordance with the present invention. The spout 37 then extends into the lumen of stem 82.

The T-shaped passage through the valve is oriented so that, when the valve handle is in the solid-line position of FIG. 8, tubes 80 and 75 communicate through the valve. When the handle is in the phantom line position, there is communication between stems 72 and 82, permitting a needle or spout to be inserted into stem 82 to sample blood or other fluid in the valve. The handle can typically be moved also to the opposite side (alongside stem 77) so that fluid from the other tube can be sampled. As with the other arrangements, the coupling bell 32 allows the syringe associated therewith to be safely and easily connected to the valve for fluid-tight taking of the desired sample.

An alternative locking arrangement is shown in FIGS. 9 and 10. As with the latch mechanism of FIGS. 4 and 5, the latching arrangement of FIGS. 9 and 10 is for the purpose of keeping the telescopic sleeves, identified as 22a and 28a in this embodiment, in the fully telescoped position with the internal spring compressed. In this embodiment, portion 34 of coupling bell 32 is provided with three axial extensions 90, 91 and 92 which protrude toward the syringe end of the apparatus. Each of these extensions occupies about 60° of arc and the extensions are substantially uniformly spaced apart. At the distal end of each extension 90-92 is an inwardly protruding bead 95, best seen in FIG. 9.

At the distal end of sleeve 22a are three uniformly spaced outwardly protruding beads 97, 98 and 99 positioned to cooperate with beads 95 on extensions 90-92, respectively. When the spring is fully compressed, the beads on the extensions and those on sleeve 22a engage in the position shown in FIGS. 9 and 10, inhibiting separation of sleeves 22a and 28a. However, when the sleeves are rotated relative to each other, beads 97-99 are moved into the gaps between extensions 90-92 and the sleeves are free to move to their extended position under the force of spring 26.

An arrangement for controlling the relative rotation of sleeves 22a and 28a is shown in FIG. 11. In this embodiment, sleeve 22a is provided with a slot 102 and the outer surface of sleeve 28a carries a key 104. Slot 102 is substantially equal in width to key 104 for a portion of its length nearest the end of the sleeve and then widens to a portion 106 which is two to four times the width of the key. The slot is dimensioned so that key 104 is in wide portion 106 only when the sleeves are in their fully telescoped position in which the sleeves are latched together if the embodiment is provided with a latch arrangement such as that shown in FIGS. 9 and 10, for example. Relative rotation between the sleeves is thus substantially prevented by the key and slot in any other than the fully compressed condition, allowing the bell 32 to be rotated by turning the syringe. Rotation of the syringe in the fully telescoped position, however, allows release of the latching arrangement by interdigitating beads 97-99 and extensions 90-92, as described above.

As will be recognized by those skilled in the art from the foregoing discussion, the present invention provides a sheathed, automatically retractable and universally adaptable needle system capable of engaging any female (fanged) Luer-Lock ® port, the female end of an IV needle system, the rubber Y injection port of an IV administration set or a needleless valve on a medication vial and may also be used, with a modified longer needle and sleeve system, to administer intramuscular, subcutaneous or intradermal medications. It can be used to administer fluids, medications, blood or blood components and an be used to "draw up" medications or other fluids or to withdraw blood from an IV catheter/needle assembly. It can be used to administer IV "piggyback" or secondary administration of fluids or medications.

The needle of the structure of the invention remains sheathed unless the system is purposefully compressed such that the locking system discussed in connection with FIG. 4 is engaged, in which case it can be used with the needle in its fully extended position with a secondary "piggy-back" administration set, but when the bell is rotated to be removed from the injection port, the locking system is released, enabling the automatic needle retraction mechanism to function.

Figure 12:
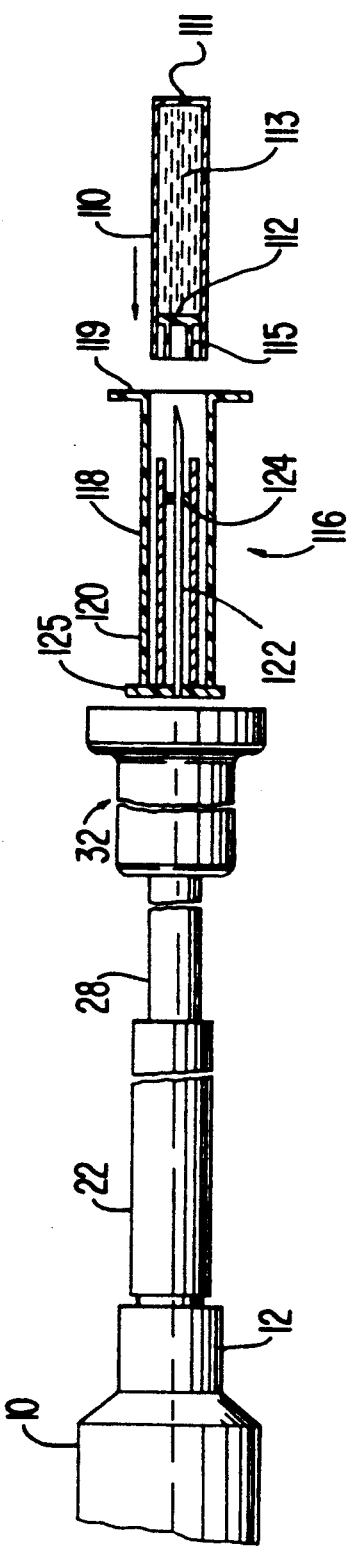
FIG. 12 is a side elevation, in partial section, of an apparatus in accordance with the invention used in combination with a syringe-injector device.

FIG. 12 shows an apparatus of the invention used with a two-part syringe injector device shown in a schematic and simplified form. This device includes a syringe medication vial 110 which typically is a cylindrical vial having an end wall 111 and containing a stopper 112. The vial is filled with a medication 113 which is to be administered by a syringe. Stopper 112 has a circular body which fits snugly in the vial and an axial extension 115.

The medication vial is used with a needle-syringe injector indicated generally at 116 which has an outer cylindrical sleeve 118, an inner cylindrical sleeve 120, a needle 122 and a fixed stop 124 which surrounds needle 122 and is fixedly held at a predetermined axial location within sleeve 120. It will be observed that the inner surface of sleeve 118 is larger than the outer surface of vial 110, but that vial 110 is larger in diameter than inner sleeve 120 so that the vial can slip between the two sleeves of injector 116. Also, sleeve 118 has a flange or flanges 119 at one end so that, in use, a person's first and second fingers can be braced against the flange while the thumb is against end wall 111 of the vial, much like using a syringe, so that the thumb can force the vial into the space between sleeves 118 and 120. Also, flanges 125 are provided at the other end, these flanges being dimensioned to form the female portion of a Luer-Lok ® fitting so that the injector can be securely attached to bell 32 of the apparatus of the invention.

The vial and injector are provided in sterile packages which are removed for use. Injector 116 is attached to bell 32 and vial 110 is inserted into the end of sleeve 118 and pushed so that the sharp end of needle 122 penetrates stopper 112, allowing medication 113 to begin entering the needle. Vial 110 is then pushed further into the injector so that extension 115 abuts stop 124. As the vial is pushed still further, stopper 112 is caused to move along the inside of vial 110 toward wall 111, becoming a piston and forcing medication 113 into and through needle 122.

Meanwhile, the medication under pressure enters needle 116 of the retractable needle assembly and passes through to the syringe. The plunger of syringe 10, which is not illustrated but which is a conventional syringe plunger, is either allowed to retract under the fluid pressure or is assisted as vial 110 is pushed in, filling the syringe with the medication. After stopper/piston 112 has reached the end of its travel at wall 111, the plunger of syringe 10 can be withdrawn a small amount more to draw in the last of the medication. Injector 116 is then uncoupled from bell 32 and the filled syringe 10 is ready to apply the medication in any of several ways, some of which have been described herein, either to a patient directly or via a coupling, Y-connector, or valve as described above.

While certain advantageous embodiments have been chosen to illustrate the invention, it will be understood by those skilled in the art that various changes and modifications can be made therein without departing from the scope of the invention as defined in the appended claims.

What is claimed is:

1. A needle shielding and use-facilitating apparatus comprising the combination of
    a first sleeve having coupling means at one end thereof for attachment of said sleeve to the output end of a fluid source;
    a hypodermic needle carried by said first sleeve, said needle having a lumen therethrough communicating at said one end with said coupling means, said needle having a pointed end portion extending beyond an opposite end of said first sleeve;
    a second sleeve having a first end telescopically and slidably received in said opposite end of said first sleeve and a second end, said second sleeve surrounding said end portion of said needle extending beyond said opposite end, said second sleeve being movable between a first position in which said end portion is totally enclosed within said second sleeve and a second position in which part of said end portion protrudes beyond said second end of said second sleeve;
    spring means within said first sleeve urging said second sleeve to said first position; and
    an end coupling attached to said second end of and movable with said second sleeve, said end coupling having means for attaching selectively to one of a plurality of articles puncturable with said needle, the length of said second sleeve being selected so that said pointed end extends into said end coupling in said second position whereby a membrane in the selected one of said articles is puncturable by said needle.

2. An apparatus according to claim 1 wherein said end coupling includes threads for attachment to a needle fitting.

3. An apparatus according to claim 1 wherein said means for attachment on said first sleeve includes a bell for attachment to a medication bottle.

4. An apparatus according to claim 1 including means for latching said first and second sleeves in said second position and for releasing said sleeves upon relative rotation of said sleeves, permitting automatic retraction of said needle.

5. An apparatus according to claim 4 and including means for inhibiting relative rotation between said first and second sleeves.

6. An apparatus according to claim 1 and including an elastomeric diaphragm within said end coupling positioned so that said pointed end of said needle passes through said diaphragm and forms a fluid tight seal therewith, preventing passage of fluids along said needle toward said fluid source.

7. An apparatus according to claim 1 wherein said fluid source is a syringe.

8. A needle shielding and use-facilitating apparatus comprising the combination of;
- a first sleeve having coupling means at one end thereof for attachment of said sleeve to a syringe;
- a hypodermic needle carried by said first sleeve, said needle having a lumen therethrough communicating at said one end with said coupling means, said needle having a pointed end portion extending beyond an opposite end of said first sleeve;
- a second sleeve having a first end telescopically and slidably received in said opposite end of said first sleeve and a second end, said second sleeve surrounding said end portion of said needle extending beyond said opposite end, said second sleeve being movable between a first position in which said end portion is totally enclosed within said second sleeve and a second position in which part of said end portion protrudes beyond said second end of said second sleeve, the length of said needle being selected so that a portion of predetermined length protrudes beyond an end coupling in said second position, whereby intramuscular injection to a predetermined depth can be accomplished with said needle, said needle being retracted when said needle is withdrawn from the muscle; and
- spring means within said first sleeve ring said second sleeve to said first position to retract said needle,
- said end coupling being attached to said second end of said second sleeve and movable with said second sleeve, said end coupling having means for attaching selectively to one of a plurality of articles puncturable with said needle, the length of said second sleeve being selected so that said pointed end extends through said end coupling in said second position whereby a membrane in the selected one of said articles is puncturable by said needle.

9. A needle shielding and use-facilitating apparatus comprising
- a first sleeve having coupling means at one end thereof for attachment of said sleeve to the output end of a fluid source;
- a hypodermic needle carried by said first sleeve, said needle having a lumen therethrough communicating at said one end with said coupling means, said needle having a pointed end portion extending beyond an opposite end of said first sleeve;
- a second sleeve having a first end telescopically and slidably received in said opposite end of aid first sleeve and a second end, said second sleeve surrounding said end portion of said needle extending beyond said opposite end, said second sleeve being movable between a first position in which said end portion is totally enclosed within said second sleeve and a second position in which part of said end portion protrudes beyond said second end of said second sleeve;
- spring means within said first sleeve urging said second sleeve to said first position to retract said needle;
- an end coupling attached to said second end of and movable with said second sleeve, said end coupling having means for attaching selectively to one of a plurality of articles puncturable with said needle, the length of said second sleeve being selected so that said pointed end extends into said end coupling in said second position whereby a membrane in the selected one of said articles is puncturable by said needle;
- an injector module having inner and outer concentric sleeves, means at one end of said module for connection to said end coupling, a stop member in said inner sleeve and a second axially extending needle; and
- a medication vial having at one end a stopper closing said vial and enclosing a fluid in said vial, said stopper having an axial extension protruding away from said fluid, said stopper being axially movable in said vial, said vial being insertable between said sleeves so that said needle penetrates said stopper and said extension abuts said stop and pushes said stopper along said vial, thereby forcing said fluid through said second needle and into said end coupling for delivery into said syringe.

* * * * *